United States Patent [19]
Stearns

[11] Patent Number: 5,424,946
[45] Date of Patent: Jun. 13, 1995

[54] ADAPTIVE ANGULAR TRANSMISSION FILTER FOR PET SCANNER

[75] Inventor: Charles W. Stearns, Milwaukee, Wis.

[73] Assignee: General Electric Company, Milwaukee, Wis.

[21] Appl. No.: 234,093

[22] Filed: Apr. 28, 1994

[51] Int. Cl.⁶ .................. G06F 15/42; G01T 1/161
[52] U.S. Cl. ................. 364/413.13; 364/724.19; 250/363.07
[58] Field of Search ............ 364/413.13, 413.14, 364/413.24, 724.01, 724.05, 724.19; 250/363.04, 363.07; 378/156

[56] References Cited

U.S. PATENT DOCUMENTS

| | | | |
|---|---|---|---|
| 4,792,900 | 12/1988 | Sones et al. | 364/413.23 |
| 5,241,181 | 8/1993 | Mertens et al. | 250/363.03 |
| 5,272,343 | 12/1993 | Stearns | 250/363.03 |
| 5,272,344 | 12/1993 | Williams | 250/363.03 |
| 5,276,614 | 1/1994 | Heuscher | 364/413.16 |
| 5,331,553 | 7/1994 | Muehllehner et al. | 364/413.24 |

Primary Examiner—David M. Huntley
Attorney, Agent, or Firm—Quarles & Brady

[57] ABSTRACT

A positron emission tomography scanner detects coincident annihilation events occurring in the field of view of a detector array and stores them as a two-dimensional sinogram array. Prior to image reconstruction, the sinogram transmission data is filtered along both dimensions (R, $\theta$) to improve image quality. Row direction (R) filtering is manually selected, and column direction ($\theta$) filtering is calculated automatically as a function of the amount of row direction filtering selected and the size of the object being imaged relative to the scanner's field of view.

5 Claims, 2 Drawing Sheets

ADAPTIVE ANGULAR TRANSMISSION FILTER FOR PET SCANNER

BACKGROUND OF THE INVENTION

The field of the invention is positron emission tomography (PET) scanners, and particularly the filtering of acquired transmission data used to reconstruct an image.

Positrons are positively charged electrons which are emitted by radionuclides that have been prepared using a cyclotron or other device. These are employed as radioactive tracers called "radiopharmaceuticals" by incorporating them into substances, such as glucose or carbon dioxide. The radiopharmaceuticals are injected in the patient and become involved in such processes as blood flow, fatty acid, glucose metabolism, and protein synthesis.

As the radionuclides decay, they emit positrons. The positrons travel a very short distance before they encounter an electron, and when this occurs, they are annihilated and converted into two photons, or gamma rays. This annihilation event is characterized by two features which are pertinent to PET scanners—each gamma ray has an energy of 511 keV and the two gamma rays are directed in nearly opposite directions. An image is created by determining the number of such annihilation events at each location within the field of view.

The PET scanner includes one or more rings of detectors which encircle the patient and which convert the energy of each 511 keV photon into a flash of light that is sensed by a photomultiplier tube (PMT). Coincidence detection circuits connect to the detectors and record only those photons which are detected simultaneously by two detectors located on opposite sides of the patient. The number of such simultaneous events indicates the number of positron annihilations that occurred along a line joining the two opposing detectors. Within a few minutes hundreds of millions of events are recorded to indicate the number of annihilations along lines joining pairs of detectors in the ring. These numbers are sorted into an array known in the art as a "sinogram", in which each row records the events at a particular view angle ($\theta$) and each column records events at a particular distance (R) from the isocenter. These numbers are corrected for system errors and employed to reconstruct an image using well known computed tomography techniques.

Filtering of transmission data along the sinogram row direction (R) is often employed to improve transmission statistics, and to thereby reduce the variance of the transmission data and improve the quality of the reconstructed emission image. However, this filtering leads to systematic errors in the attenuation correction and it is common practice to provide the operator with control of a filter parameter so that he may make the tradeoff between noise reduction in the image and the introduction of systematic errors. The choice will be determined by imaging circumstances and a filter parameter, such as filter width in millimeters, is adjusted by the operator to optimize the image. The effect of this filtering in the row direction (R) is uniform throughout the field of view and is, therefore, relatively easy to predict.

Transmission statistics can also be improved by filtering the transmission data in the sinogram in the column direction ($\theta$). However, the resolution impact of filtering in the $\theta$ direction is less at the center of the field of view than at the edges, and this makes the selection of a filter in any given situation more complex. As a result, PET scanners typically do not enable the operator to select filter parameters for $\theta$ direction filtering because the impact on the resulting image is too complex.

SUMMARY OF THE INVENTION

The present invention relates to a PET scanner, and particularly, to an improved filter for both the row direction (R) and column direction ($\theta$) of the sinogram transmission data. More particularly, the width of the filter in the column direction ($\theta$) is determined automatically as a function of the selected row direction (R) filter width and as a function of the object size relative to the total field of view. The size of the object is measured by examining the sinogram transmission data, and the row direction (R) filter width is input from the operator work station. A view reduction factor ($\alpha$) is calculated, and one of a plurality of column direction ($\theta$) filters is selected from a stored table using this view reduction factor ($\alpha$).

A general object of the invention is to automatically select a column direction ($\theta$) filter which improves image quality under a wide range of operating conditions. It has been discovered that the amount of column direction ($\theta$) filtering that can be applied without noticeably reducing image resolution is directly related to the amount of row direction (R) filtering selected by the operator. In addition, more filtering can be applied without noticeable reduction in image resolution if the object being imaged occupies a smaller portion of the scanner's total field of view.

Yet another object of the invention is to provide column direction ($\theta$) filtering without further complicating the operation of the PET scanner. The operator need only select the row direction (R) filter parameter and the present invention enables the column direction ($\theta$) filter parameter to be determined automatically.

DESCRIPTION OF THE PREFERRED EMBODIMENT

Figure 1:
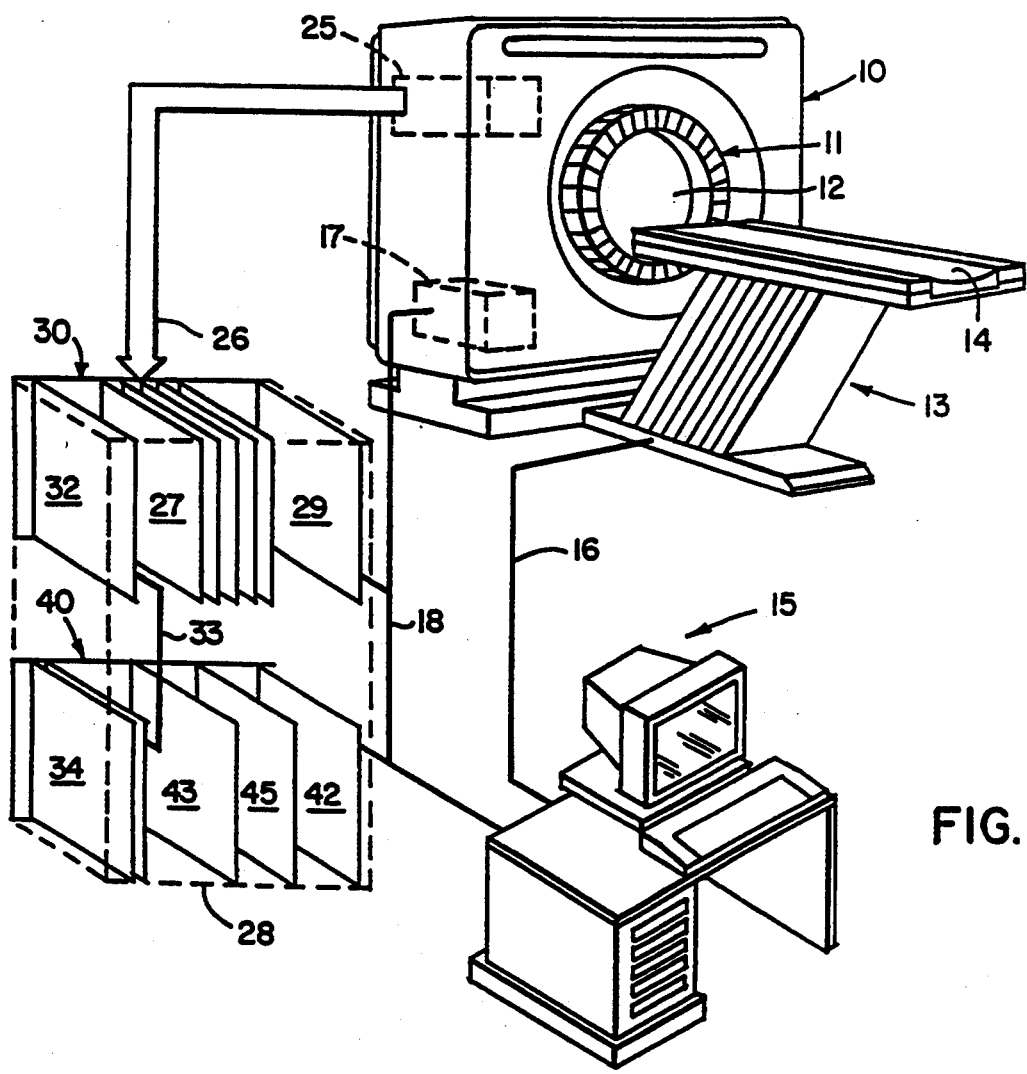
FIG. 1 is a pictorial view with parts cut away of a PET scanner system which employs the present invention.

Referring particularly to FIG. 1, the PET scanner system includes a gantry 10 which supports a detector ring assembly 11 about a central opening, or bore 12. A patient table 13 is positioned in front of the gantry 10 and is aligned with the central axis of the bore 12. A patient table controller (not shown) moves the table bed 14 into the bore 12 in response to commands received from an operator work station 15 through a serial communications link 16. A gantry controller 17 is mounted within the gantry 10 and is responsive to commands received from the operator work station 15 through a second serial communication link 18 to operate the gantry.

Figure 3:
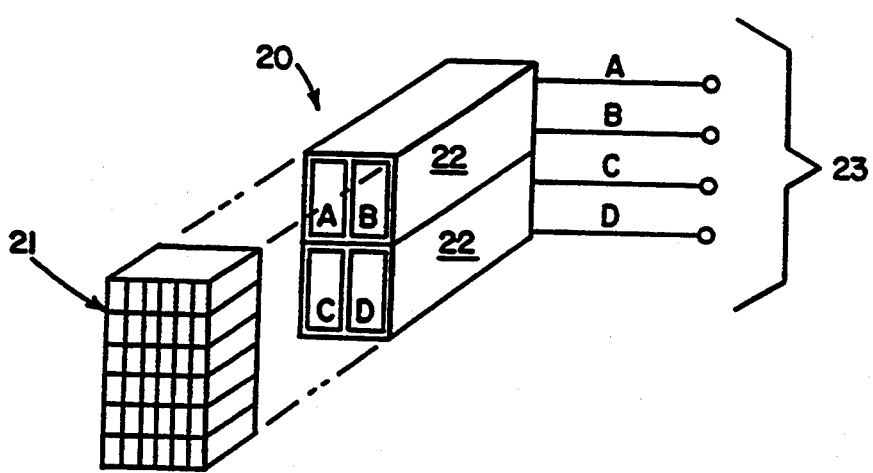
FIG. 3 is a pictorial view of a detector unit which forms part of the PET scanner system of FIG. 1.
Figure 2:
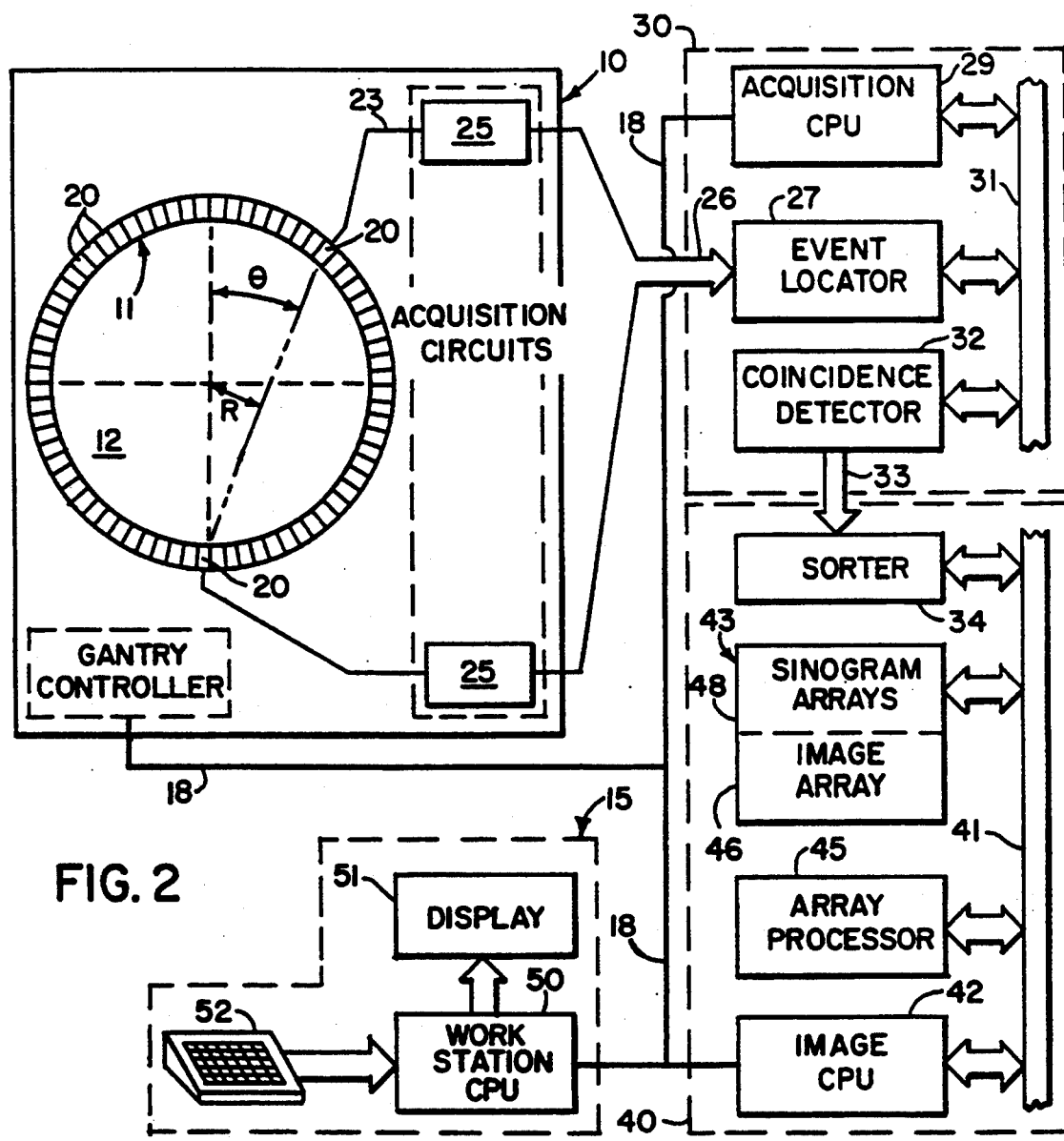
FIG. 2 is a schematic diagram of the PET scanner system of FIG. 1.

As shown best in FIGS. 2 and 3, the detector ring 11 is comprised of 112 detector units 20. Each unit 20 includes a set of scintillator crystals 21 (abbreviated BGO) arranged in a matrix and disposed in front of four photomultiplier tubes 22 (abbreviated PMT). Each PMT 22 produces an analog signal on line 23 when a scintillation event occurs. A set of acquisition circuits 25 are mounted within the gantry 10 to receive these signals and produce digital signals indicating the event coordinates (x,y) and the total energy. These are sent through a cable 26 to an event locator circuit 27 housed in a separate cabinet 28. Each acquisition circuit 25 also produces an event detection pulse (EDP) which indicates the exact moment the scintillation event took place.

Referring particularly to FIGS. 1 and 2, the event locator circuits 27 form part of a data acquisition processor 30 which periodically samples the signals produced by the acquisition circuits 25. The processor 30 has an acquisition CPU 29 which controls communications on the local area network 18 and a backplane bus 31. The event locator circuits 27 assemble the information regarding each valid event into a set of digital numbers that indicate precisely when the event took place and the position of the BGO crystal 21 which detected the event. This event data packet is conveyed to a coincidence detector 32 which is also part of the data acquisition processor 30.

The coincidence detector 32 accepts the event data packets from the event locators 27 and determines if any two of them are in coincidence. Coincidence is determined by a number of factors. First, the time markers in each event data packet must be within 12.5 nanoseconds of each other, and second, the locations indicated by the two event data packets must lie on a straight line which passes through the field of view (FOV) in the scanner bore 12. Events which cannot be paired are discarded, but coincident event pairs are located and recorded as a coincidence data packet that is conveyed through a serial link 33 to a sorter 34. For a detailed description of the coincidence detector 32, reference is made to U.S. Pat. No. 5,241,181 entitled "Coincidence Detector For A PET Scanner" which is incorporated herein by reference.

The sorter 34 forms part of an image reconstruction processor 40. The sorter 34 counts all events occurring along each projection ray (R,$\theta$) and organizes them into a two dimensional sinogram array 48 which is stored in a memory module 43. For a detailed description of the sorter 34, reference is made to U.S. Pat. No. 5,272,343 entitled "Sorter For Coincidence timing Calibration In A PET Scanner" which is incorporated herein by reference.

The image reconstruction processor 40 also includes an image CPU 42 that controls a backplane bus 41 and links it to the local area network 18. An array processor 45 connects to the backplane 41 and it reconstructs images from the sinogram arrays 48 after the transmission data therein has been corrected and then filtered in accordance with the teachings of the present invention. Corrections are made to offset measurement errors such as those caused by attenuation of the gamma rays by the patient, detector gain nonuniformities, random coincidences, and integrator deadtime. The corrected sinogram array 48 is then Fourier transformed by the array processor 45 and multiplied by a two-dimensional filter kernel array selected according to the present invention. The filtered data is then inverse Fourier transformed, and each resulting filtered array element is then back projected to form the image array 46. The resulting image array 46 is stored in memory module 43 and is output by the image CPU 42 to the operator work station 15.

The operator work station 15 includes a CPU 50, a CRT display 51 and a keyboard 52. The CPU 50 connects to the local area network 18 and it scans the keyboard 52 for input information. Through the keyboard 52 and associated control panel switches, the operator can control the calibration of the PET scanner, its configuration, and the positioning of the patient table for a scan. Similarly, the operator can control the display of the resulting image on the CRT display 51 and perform image enhancement functions using programs executed by the work station CPU 50. One of the configuration elements input by the operator is the radial filtering width $r_f$ which selects the size of the filter kernel array along the row dimension (R) of the sinogram array 48.

It is well known that the number of independent angular views needed for an accurate representation of an object is directly proportional to the diameter of the field of view (bigger object, more views needed) and inversely proportional to image resolution (smaller details, more views), or:

$$N_{views} \alpha \frac{D}{r} \qquad (1)$$

where D is the diameter of the field of view and r is the image resolution. The most stringent requirement occurs when high resolution is required in a reconstruction of the maximum field of view of the scanner.

A reduction in imaging field of view or resolution degradation (by filtering, for example) can be interpreted as relaxing the requirements for angular views. This may be quantified by computing a view reduction factor relative to the worst case situation:

$$\alpha = \frac{N_0}{N_1} = \frac{D_0}{D_1} \frac{r_1}{r_0}, \qquad (2)$$

where the "0" condition represents the most stringent case and the "1" condition represents the less stringent imaging situation. If the resolution degradation is achieved by projection filtering with a kernel $r_f$ then $r_1$ may be estimated by adding $r_0$, the resolution of a unfiltered reconstruction, and $r_f$ is quadrature. In that event, the view reduction factor may be expressed as:

$$\alpha = \frac{D_0}{D_1} \sqrt{1 + \left(\frac{r_f}{r_0}\right)^2} . \qquad (3)$$

The filter kernel for the $\theta$ dimension is chosen based on this value of $\alpha$. At one extreme, for example, if the object occupies the entire field of view (i.e. $D_1=D_0$) and no filtering is applied in the row dimension R (i.e. $r_f=0$), then $\alpha=1$ and no filtering is applied in the $\theta$ direction. As $\alpha$ increases, more filtering can be applied in the $\theta$ direction without causing image artifacts. In the preferred embodiment, a table of filter kernels is stored in the memory module 43 as a function of values for $\alpha$. The image CPU 42 calculates $\alpha$ according to equation (3), and the value of $\alpha$ is used to look up the appropriate $\theta$ filter kernel. This is combined with the manually selected row dimension filter kernel to form the 2D filter used to filter the sinogram array 48 as described above.

TABLE 1

| α | θ Kernel |
|---|---|
| $1.0 \leq \alpha < 1.75$ | [1] |
| $1.75 \leq \alpha < 2.50$ | [⅓, ⅓, ⅓] |
| $2.50 \leq \alpha$ | [1/5, 1/5, 1/5, 1/5, 1/5] |

Table 1 shows the mapping of α to filter kernels recommended for the preferred embodiment of this invention. The table has been designed so that a moderate amount of transmission filtering (such as $r_f = 8$ mm, giving $\alpha = 1.94$ for a full field of view image) yields a three point averaging kernel, while heavy transmission filtering ($r_f = 12$ mm, $\alpha = 2.69$) results in a five point kernel. This may be considered a slightly conservative filter choice, since five row filtering does not cause any image artifacts in clinical examples under these conditions. Other filter kernels having an odd number of points that are symmetrical about its center and having a total weight of 1.0 may be used in this stored table.

In the preferred embodiment α was calculated using equation three, and the PET scanner of the preferred embodiment has a field of view ($D_0$) of 550 mm and an intrinsic resolution ($r_0$) of 4.8 mm. The object field of view ($D_1$) is determined by examining the transmission sinogram 48 and estimating the distance $D_1$ between detected edges. The object edges are estimated by examining several sinogram rows for the first and last points having attenuation values greater than 30%, which corresponds to about 37 mm of water-equivalent attenuation. The edges furthest from the sinogram center are selected, and the distance between them is used as the distance $D_1$.

I claim:

1. A positron emission tomography scanner the combination comprising:

detector means for detecting coincident photons produced by annihilation events occurring within an object located within a field of view of the scanner, a sorter for determining the location (R,θ) of each detected annihilation event and storing an indication thereof as transmission data in a two-dimensional sinogram array;

input means for receiving an indication of the amount of row direction (R) filtering ($r_f$) to be applied to the transmission data stored in the sinogram array;

calculation means coupled to the input means and the sinogram array for determining the amount of column direction (θ) filtering to be applied to the transmission data stored in the sinogram array as a function of the amount of row direction filtering ($r_f$) and as a function of the size of the object located within the field of view of the scanner;

means for filtering the transmission data stored in the sinogram array in both the row direction (R) and column direction (θ) by the amounts indicated by the input means and the calculation means; and image reconstruction means for producing an image array from the filtered transmission data in the sinogram array.

2. The positron emission tomography scanner as recited in claim 1 in which the calculation means determines the amount of column direction (θ) filtering by calculating a view reduction factor (α) in accordance with the following expression:

$$\alpha = \frac{D_0}{D_1} \sqrt{1 + \left(\frac{r_f}{r_0}\right)^2}$$

where $D_0$ = scanner field of view diameter,
$D_1$ = object diameter,
$r_0$ = intrinsic resolution of scanner, and the value of the view reduction factor (α) is used to determine the amount of column direction (θ) filtering.

3. The positron emission tomography scanner as recited in claim 2 which includes means for storing a plurality of filter kernels and the calculating means selects one of said filter kernels in response to the value of the calculated view reduction factor (α).

4. The positron emission tomography scanner as recited in claim 3 in which the means for filtering employs the selected filter kernel to filter the transmission data in the column direction.

5. The positron emission tomography scanner as recited in claim 2 in which the calculation means determines object size $D_1$ by analyzing the transmission data stored in the sinogram array.

* * * * *